United States Patent [19] [11] 4,292,310
Gordon et al. [45] Sep. 29, 1981

[54] METHOD OF TREATING HYPERCHOLESTEROLEMIA WITH N-ACYL AMPHOTERICIN B

[76] Inventors: Harry W. Gordon, 210 E. 181st St., Bronx, N.Y. 10457; Carl P. Schaffner, 10 Youngs Rd., Trenton, N.J. 08619

[21] Appl. No.: 29,198

[22] Filed: Apr. 12, 1979

Related U.S. Application Data

[60] Division of Ser. No. 794,920, May 9, 1977, Pat. No. 4,163,050, which is a division of Ser. No. 521,289, Nov. 6, 1974, Pat. No. 4,039,659, which is a division of Ser. No. 177,512, Sep. 2, 1971, Pat. No. 3,855,409, which is a continuation of Ser. No. 221,062, Jan. 26, 1972, Pat. No. 3,966,910, and a continuation of Ser. No. 24,797, Apr. 1, 1970, abandoned, which is a continuation of Ser. No. 627,313, Mar. 31, 1967, Pat. No. 3,627,879.

[51] Int. Cl.$^3$ ............................................. A61K 35/00
[52] U.S. Cl. ............................................. 424/122
[58] Field of Search ........................................ 424/122

[56] References Cited

U.S. PATENT DOCUMENTS 3,244,590  4/1966  Schaftner et al. ................... 424/122

Primary Examiner—Jerome D. Goldberg
Attorney, Agent, or Firm—Darby & Darby

[57] ABSTRACT

Orally administered compositions for altering liquid metabolism are described herein, these compositions containing an effective dose of n-acyl amphotericin B. Also the method of altering lipid metabolism including reducing and controlling the blood cholesterol level, is described herein.

3 Claims, No Drawings

METHOD OF TREATING HYPERCHOLESTEROLEMIA WITH N-ACYL AMPHOTERICIN B

This application is a divisional of copending application Ser. No. 794,920 filed May 9, 1977 (now U.S. Pat. No. 4,163,050), which is a divisional of application Ser. No. 521,289 filed Nov. 6, 1974 (now U.S. Pat No. 4,039,659), which is a division of application Ser. No. 177,512 filed Sep. 2, 1971 (now U.S. Pat. No. 3,885,409), which is a continuation of application Ser. No. 221,062 filed Jan. 26, 1972 (now U.S. Pat. No. 3,966,910), and a continuation of application Ser. No. 24,797 filed Apr. 1, 1970 (abandoned) which is a continuation of application Ser. No. 627,313 filed Mar. 31, 1967 (now U.S. Pat. No. 3,627,879).

This invention relates to a composition containing a polyenic macrolide compound and the method of altering lipid metabolism by orally administering the same.

The implication of the blood lipids as a contributing factor in the functioning of the highly vascularized organs such as the kidneys, liver, brain, lungs, testes, heart, and other organs requiring smooth, free, sufficient blood flow has contributed to the intensive and vigorous research for agents, that will control the lipid content, including triglycerides, cholesterol, lipoproteins, etc., in the blood stream and tissues. A majority of studies have focused on cholesterol because of the substantial evidence available relating blood cholesterol levels to conditions such as atherosclerosis, arteriosclerosis and other schlerotic conditions, coronary heart disease, cerebral hemorrhage, liver and kidney dysfunction associated with vascular obstruction, sterol calculi resulting from hypercholesterolemia, etc.

Diseases such as arteriosclerosis, which is a generic term for a number of chronic pathologic conditions, affect the intima or the media of arteries and is characterized by thickening, hardening and loss of elasticity of vessel walls, with resultant alteration in size of the lumen. Atherosclerosis, which is a form of arteriosclerosis characterized by intimal thickening due to localized accumulations of lipids, known as atheromas. Atherosclerosis is of great importance because of its predilection for coronary (cerebral) and peripheral arteries. It develops insidiously, probably due to multiple factors (metabolic, humoral and hemodynamic being of primary significance).

The earliest lesions of atherosclerosis are the subintimal fatty streaks seen in the thoracic aorta in young mammals, which either retrogress or grow larger, forming plaques. While these may involve any artery, they are most common in the aorta, coronary, cerebral, and peripheral arteries of the lower extremities. Subintimal hemorrhage or ulceration of the plaque may lead to thrombosis and occlusion of the involved vessel, resulting in a variety of symptoms and signs due to ischemia.

It is believed that B-lipoproteins are basically responsible for the disease process. These lipoproteins are a heterogeneous family of macromolecules containing protein, cholesterol, phospholipids and triglycerides in varying proportions. The chemical measurement of any of these lipids is an index of the accumulation of lipoproteins of a given density. These lipoproteins, which are essential but not solely sufficient to cause disease, interact with the arterial wall in such a way as to produce the discrete intimal lesion.

The most frequent and important cause of acute renal failures (dysfunction) is acute tubular necrosis (lower nephron nephrosis or kidney shutdown). Although the causes advanced for this condition are numerous it is postulated that lipoid material depositing on the capillary walls may also contribute. Functional renal disorders are also associated with arteriolar nephrosclerosis which consists of sclerosis of the small renal arterioles. There is also interference with the normal function of the kidney in cases of atherosclerosis in which there is a thickening of the peripheral arteries due to localized accumulations of lipids known as atheromas.

Liver dysfunction associated with vascular obstruction is often seen in obese mammals in whom it is due to excessive fat intake. Fatty infiltration of the liver can also be caused by numerous factors including chronic infections (e.g., tuberculosis), metabolic disorders (e.g. diabetes mellitus), etc. In these conditions, fatty liver probably is due to migration of fat from storage deposits.

There has also been in recent years increasing interest in the formulation of "fat-free" diets in order to control obesity and/or the amount of lipids, including cholesterol, present in the blood stream as it is well known that the ingestion of fats is one means of increasing the amount of lipids in the blood. There has been much publicity of the fact that the ingestion of fat, which essentially consists of glycerol esters of higher fatty acids which break down in the digestive tract, must be maintained at a minimum in cases where a high lipid metabolism is considered dangerous.

Despite intensive research for hypolipiodal agents, including hypocholesterolemic agents, relatively few compounds have been found which are acceptable for long-term use and even these have drawbacks. For example, natural and synthetic estrogens are known to inhibit cholesterol induced atherosclerosis in mammals. In general, however, the undesirable feminizing side effects of estrogens limit their usefulness in male mammals. These side effects have stimulated a search for "non-estrogenic estrogens" (compounds in which the sterolic effect has been separated from the estrogenic effect) but to date no useful agent has been discovered. Other hypocholesterolemic agents have met with varying degrees of success but undesirable side effects have been encountered. In addition, the use of a fat-free diet to alter the lipiodal metabolism has obvious limitations because fat is used extensively in the preparation of many foods and hence such a diet is extremely difficult to maintain.

It has now been unexpectedly discovered that the oral administration in a solid pharamaceutical formulation of a composition containing n-acyl amphotericin B will be effective in altering lipid metabolism, including reducing and/or controlling triglycerides, cholesterol, lipoproteins, etc. in mammals, thereby providing an agent useful for the treatment of those conditions believed associated with the lipid metabolism, e.g., hypercholesterolemia and other conditions mentioned heretofore. This discovery is particularly surprising because it has been suggested in the prior art that "Mycostatin" (trademark for nystatin), a polyenic macrolide compound having four conjugated double bonds is ineffective on the serum cholesterol (Steiner et al, *Circulation* Vol. 24, pp. 729-735 (1961)).

The action of the compounds of this invention is believed not due to the antibiotic function of the polyenic macrolide compounds which have been previously described in the art, but apparently to their chemical structure.

Accordingly, one aspect of the present invention is to provide a method for altering lipid metabolism which comprises orally administering an effective dose of n-acyl amphotericin B a specific known polyenic macrolide compound.

Another aspect of the present invention is to provide an orally administered composition for altering lipid metabolism which composition comprises a solid pharmaceutical formulation comprising an effective dose of n-acyl amphotericin B a specific known polyenic macrolide compound.

An additional aspect of the present invention is to provide an enteric tablet or capsule containing an effective dose of a composition of the present invention for altering the lipid metabolism.

Other aspects of the invention will be apparent from the following detailed description.

As used herein, the reduction of sterol levels is intended to include the treatment of hypersterolemia, e.g., hypercholesterolemia, as well as conditions believed associated directly or indirectly with hypersterolemia.

According to the present invention, the compositions found effective for altering lipid metabolism in mammals comprise n-acyl amphotericin B.

Since the polyenic compounds were first discovered in 1950, a large body of literature has become available describing the extensive chemical investigation of these compounds and demonstrating that they possess generally similar chemical properties. The present broad classification of the polyenic macrolide compounds is due to the work of Oroshnik et al, in 1955 (see Polyene Antibiotics, Science, Vol. 121, pp. 147-149). In 1955 only nine polyenic macrolide compounds had been isolated in reasonably pure form but since then well over fifty polyenic macrolide compounds have been reported. Undoubtedly some of these polyenes have been reported more than once under different names.

The known polyenic macrolide compounds have been produced as antibiotics by cultivation of Streptomyces in different media and by extraction of the substances from these cultures. It has been demonstrated in the literature that the known polyenic compounds are (1) of fairly high molecular weight (ca 700-1500), (2) contain macrocylic lactones, better known as macrolides (hereinafter referred to as "polyenic macrolide compounds"), and (3) each possess a chromophore in the nucleus of from four to seven conjugated double bonds (tetraenes, pentaenes, hexaenes, and heptaenes) identified by examination of their ultra-violet absorption spectra. These conjugated systems are generally unsubstituted (except the methyl pentaenes) and either of the "all-trans" or "cis-trans" configuration. Based on the evidence available to date, it is indicated that the known polyenic macrolide compounds contain a twenty-six to a thirty-seven membered lactone ring wherein all of the ring atoms except the single oxygen atom are carbons. The evidence to date also indicates that only C, H, O, and N are present in the known polyenic macrolide compounds.

The polyenic macrolide nucleus contains a relatively planar lipophilic section (polyenic chromophore) and a less rigid hydrophilic section due to the presence of highly polar substituents, particularly hydroxyls, as well as other substituents which will be discussed in detail later herein. All of the known polyenic macrolide compounds contain at least one hydroxyl moiety and in some cases at least six hydroxyl moieties. It is difficult to estimate the precise number of hydroxyl functions present in each known polyene macrolide compound because complete, or nearly complete structures have been proposed for relatively few polyenes which are: pimaricin [Ceder et al—Acta Chem. Scand. Vol. 18, pp. 72-125 (1964)]; filipin [Cedar et al—Act Chem. Scand., Vol. 18, pp. 558-560 (1964)]; nystatin [Birch et al—Tetrahedron Letters, Vol. 23, pp. 1491-1497 (1964)]; lagosin [Dhar et al—J. Chem. Soc., p. 842 (1964)]; fungichromin [Cope et al, J. Amer. Chem. Soc., Vol. 84, pp. 2170-2178 (1962)].

The distinct sections of polar and non-polar character in the polyenic macrolide nucleus result in the unique and peculiar solubility properties exhibited by the polyenic macrolide compounds. As a group of compounds the polyene macrolides generally exhibit very poor solubility in the common organic solvents such as lower alcohols, esters, ketones, ethers, etc., and are insoluble in water. The polyenic macrolides exhibit improved solubility in mixtures of lipophilic and hydrophilic solvents, e.g., aqueous solutions of lower alcohols, and are easily soluble in aqueous pyridine. Good solubility of the polyenic macrolide compound is noted in highly polar solvents such as dimethyl sulfoxide, formamide, glacial acetic acid, etc.

Any single known polyenic macrolide compound may have substituents linked to the ring such as amino sugars and N-acyl derivatives thereof, aromatic amines and N-acyl derivatives thereof, carboxyls, methyls, carbonyls, aliphatics, hydroxy aliphatics and epoxies. The majority of the polyenic macrolides are amphoteric substances. The acidity of these polyenes is due to a carboxyl group and the basicity of the amphoteric polyenes is due to the presence of an amino sugar known as mycosamine (3-amino 3,6-dideoxy-D-mannose) or perosamine (4-amino 4,6-dideoxy-D-mannose). The basicity may also be due to the additional presence of aromatic amino moieties. Some polyene macrolides such as filipin, lagosin and fungichromin are neutral. The substitution of the amine function with such organic radicals as acyl groups reduces the effectiveness of the macrolide nucleus in altering lipid metabolism but does not destroy this activity. The acylation results in neutralization of the basic properties and improved solubilities of the N-acylated derivative in various media, such as organic solvents, and readily permits the formation of water soluble salts, as fully described in U.S. Pat. No.3,244,590.

The following articles should be consulted for references to the discovery, isolation and chemical properties of the polyenic macrolide compounds:

1. Vining, "The Polyene Antifungal Antibiotics" Hindustan Antibiotics Bull., Vol. 3, pp. 32-54 (1960).

2. Waksman et al, "The Actinomycetes, Vol. III, Antibiotics of Actinomycetes" (Williams and Wilkins, Baltimore, 1962).

3. Droughet, "Noveaux Antibiotiques Antifongiques" Symp. Int. Chimiotherapie, Naples, 1961, pp. 21-50 (1963).

4. W. Oroshnik et al, "Fortschritte der Chemie Organischer Naturstoffe" Vol. XXI, pp. 18-79 (1963).

The general class of polyenic macrolide compounds to which the present invention is applicable are the heptaenes. These compounds will now be discussed in greater detail by reference to the substances that fall within each of these three separate classifications.

The heptaene group of polyene macrolides are classifiable into at least five groups which may be correspondingly identified as follows:

A. Aromatic I—Identified as those compounds containing the heptaene macrolide nucleus, one carboxyl group, a single amino sugar moiety (mycosamine) glycosidically linked to the macrolide nucleus and an aromatic amino moiety (p-aminophenyl) aldolically linked to the macrolide nucleus. Representatives of this group are (a) candicidin which may possibly be identical to trichomycin A, hamycin (minor component), heptamycin, ascosin and levorin $A_2$; (b) trichomycin B which may possibly be identical to levorin $A_3$, hamycin (major component) and PA-150; and (c) levorin A.

B. Aromatic II—Identified as those compounds containing the heptaene macrolide nucleus, one carboxyl group, an amino sugar (mycosamine) glycosidically linked to the macrolide nucleus, and an aromatic amino moiety (N-methyl-p-aminophenyl) aldolically linked to the macrolide nucleus. Representative polyenic macrolides of this group are: (a) candimycin, and (b) hamycin (minor component of hamycin complex).

C. Aromatic III—Identified as those compounds containing the heptaene macrolide nucleus, an aromatic amino moiety (N-methyl-p-aminophenyl), aldolically linked to the macrolide nucleus, and an amino sugar (perosamine), glycosidically linked to the macrolide nucleus. It is noted that the aromatic amino moiety just identified has previously been incorrectly reported in the literature as a p-aminobenzyl moiety. Representative of this group is fungimycin. This substance was originally identified as antibiotic No. NC 1968 and for a brief interval identified as perimycin and aminomycin.

D. Non-Aromatic—Identified as those compounds containing the heptaene macrolide nucleus, one carboxyl moiety and a single amino sugar (mycosamine), glycosidically linked to the macrolide nucleus. Representative of this group are: (a) candidin; (b) candidinin; (c) candidoin; (d) amphotericin B; (e) mycoheptin; (f) levorin B; and (g) antibiotic F-17-C.

E. Poorly Defined Heptaenes: A number of heptaene macrolide compounds have been described in the literature but have not as yet been sufficiently characterized as to all the substituents linked to the polyenic macrolide nucleus. These heptaene macrolides are streptomyces abikoens is heptaene, aureofacin, antibiotic 757, ayfactin A, ayfactin B, antifungin 4915, eurotin A, antibiotic AE-56, antibiotic 2814-H, grubilin, monicamycin, antibiotics A, B, and C from Streptomyces species related to *S. viridans*.

It will be understood that where a polyenic macrolide compound of the class herein described is identical with one of the above named compounds, but has been known by another name by reason of independent production or production in accompaniment to other antibiotics, the identification of such substances by the name set forth above is intended to mean the same compound under all other designations.

The N-acyl derivatives of the polyenic macrolide compounds having five to seven conjugated double bonds are also useful for altering lipid metabolism in accordance with the present invention and are generally prepared by reaction of the corresponding acid anhydride with the polyenic macrolide substance. In general, the acyl derivatives are derived from monocarboxylic aliphatic acids, dicarboxylic aliphatic acids and aromatic carboxylic acids. Thus the acyl derivatives and their pharmaceutically acceptable salts, can be defined as derivatives of a polyenic macrolide compound and an organic acid, the acyl group of the acid being linked to at least one amino nitrogen of the macrolide compound. A detailed description of the preparation of N-acyl derivatives of polyenic macrolide compounds may be found, for example, in U.S. Pat. No. 3,244,590.

Examples of the various N-acyl derivatives are formyl, acetyl, propionyl, chloroacetyl (and other halogen-substituted aliphatic monocarboxylic acids), phenylacetyl, phenoxyacetyl, butyryl, valeryl, caproyl, succinyl, phthalyl, 3-nitrophthalyl, benzoyl, substituted benzoyl and the like.

The pharmaceutical compositions are formulated so as to be suitable for oral administration. The active ingredient is contained in a capsule or tablet, preferably in enteric form. The quantity of effective dose supplied by each capsule or tablet is relatively unimportant since the total dosage can be reached by administration of either one or a plurality of capsules or tablets or both. The capsules employed may comprise any well known pharmaceutically acceptable material such as gelatin, cellulose derivatives, etc. The tablets may be formulated in accordance with conventional procedure employing solid carriers, lubricants, etc., well known in the art. Examples of solid carriers are: starch, sugar, bentonite and other commonly used carriers.

The following examples illustrate suitable pharmaceutical formulations containing the compounds of this invention.

EXAMPLE 1

Hard gelatin capsule available from the Robin Pharmacal Corporation (size 00) is filled with about 0.83 grams of lactose (Fast Flow available from Foremost Dairies, Inc.) and about 100 mg. of active material, the lactose and active ingredient being triturated together in a pestle and mortar until a very fine yellow amorphous powder resulted, prior to filling of the capsule. Obviously, any desired number of capsules may be filled by mixing together any amount of lactose and active ingredient in the same weight ratio indicated above so that each capsule will contain 100 mg. active ingredient; and the quantity of active ingredient may be altered, as desired, by varying the weight ratio of the indicated materials.

EXAMPLE 2

125 g. of corn starch and 2112.5 g. lactose are dried at 140° F. for 12 hours before compounding. After drying, each of these materials is sifted through a No. 14 mesh stainless steel screen. The sifted corn starch and lactose are thoroughly mixed for 30 minutes and to this mixture there is added a blended mixture of 250 g. active ingredient and 12.5 g. magnesium stearate. This admixture is blended and then compressed on a tableting machine into 5000 substantially round tablets each containing 50 mg. active ingredient and weighing about 500 mg.

EXAMPLE 3

Enteric tablets for use in this invention may be formulated as follows:

16 g. of powdered corn starch (U.S.P. quality) is dried at 120° F. for 12 hours and passed through a No. 25 mesh stainless steel screen. The sifted corn starch is then mixed with 255 g. of anhydrous lactose (direct tablet grade). To this mixture, 4 g. of magnesium stearate is added followed by 50 g. of the active ingredient. These materials are then mixed in a small pebble mill for 30 minutes and compressed on a single punch machine producing 1,000 tablets, each containing 50 mg. active ingredient. Each tablet weighs approximately 325 mg. The average hardness is 6, as measured on a Monsanto Hardness Tester.

The tablets are then placed in a coating pan rotating at 29 r.p.m. and subjected to warm air of approximately 80° F. for about 10 minutes. Then 30 cc's of a pharmaceutical glazed composition is applied, this composition being refined wax and rosin free orange flake shellac with anhydrous alcohol as the medium therefor. Talcum (U.S.P.) or similar dusting powder is applied to the tablets to prevent the tablets from sticking to each other or to the pan and this procedure is followed after the application of each coat to the tablets. The coat is allowed to dry for approximately one hour. Thereafter three additional coats are applied in a similar manner, each coat comprising 30 cc's of the pharmaceutical glaze, with approximately one hour of drying time between the application of successive coats. After four coats are applied the tablets are dried overnight at room temperature and then four more coats are applied in the same manner using the same composition. Each coat is allowed to air dry for 3 hours before applying the next coat. Each of the 8 coats of the enteric tablets is approximately 0.001 inch in thickness. Obviously, the thickness of the coating can be controlled by varying the concentration of the pharmaceutical glaze in the alcohol medium.

The enteric tablets are tested in accordance with the in vitro disintegration test for enteric-coated tablets described in U.S.P. XVII and were found to pass this test.

While the number of coats used in the example heretofore described is 8, it will be appreciated that there are many factors to be considered which permit variation in the number of coats, including the size and shape of the tablets or capsules, the type of coat or combination of coats, etc.

Other procedures and materials well known in the prior art may be employed to prepare suitable enteric coatings. The selection of the coating substance is governed to a large extent by pH and enzyme considerations and the desire to have the enteric composition disintegrate or dissolve when it reaches the duodenum region of the intestinal tract and not in the stomach. The disintegration or dissolution of an enteric coating in the intestinal tract usually depends on several factors, the most important of which are (1) the presence of acidic groups in the enteric substance which cause it to be insoluble in the low pH environment of the stomach but soluble in the intestinal tract due to the higher (but usually not alkali) pH of the media there, and (2) the resistance of the coating to attack by oral and gastric enzymes.

Illustrative of other well known substances that may be used for the enteric coating are the following: cellulose acetate phthalate with resinous carrier; cellulose acetate phthalate-tolubalsam-shellac; cellulose acetate phthalate with fats and waxes; shellac-castor oil; ammoniated shellac; shellac-stearic acid-tolubalsam; stearic acid-castor oil over shellac-silica gel, cellulose acetate phthalates with or without plasticizer and dusting powder(s); acid phthalates of glucose, fructose, etc; ternary copolymers of styrene, methacrylic acid and butyl half-ester of maleic acid; alkyd resin-unsaturated fatty acids-shellac; polyvinyl acid phthalate, etc.

For a description of the procedure for manufacturing enteric formulations such as those exemplified heretofore, reference should be made to U.S. Pat. Nos. 2,196,768; 2,433,244; 2,455,790; 2,540,979; 2,858,252; 3,080,346 and British Pat. Nos. 760,403 and 820,495.

The effectiveness of the compounds of this invention has been indicated by tests in large mammals, i.e., those weighing at least about 1 kilogram. For example, tests conducted on dogs with candicidin demonstrates the effectiveness of the polyenic macrolide compounds including the reduction of blood cholesterol levels.

The basic procedure used for the determination of cholesterol levels is the method of J. P. Peters and D. D. Van Slyke, described in the text "Quantitive Clinical Chem." Vol. II, pp. 504–508 (Williams & Wilkins).

Average control serum lipid levels are established prior to the administration of the candicidin to the dogs which are stabilized on diet, feeding regime. After the average control serum lipid values are obtained, 20 mg/kg of body weight is orally administered twice daily, once in the morning and the second dose about 6 to 8 hours later, each dose containing 10 mg of active ingredient. After two weeks of oral administration, blood samples are tested for serum cholesterol. All blood samples are drawn for assay prior to feeding with no food (except water) for at least 12 hours. Administration of candicidin is continued and blood samples are tested again for serum cholesterol at the end of each week of administration.

While the present invention is not predicated on any present theoretical considerations, it is believed that the possible mechanism by which the compositions of this invention exhibit their action is through the formation of a complex in the intestinal tract with sterols, such as cholesterol, thus preventing absorption of the complexed sterol. Therefore, absorption of the compositions of this invention is not necessary for alteration of the lipid metabolism to occur. Initially, depleting the absorption of the sterols is likely to stimulate a release of stored materials from the tissues (fatty acids, triglycerides, sterols, etc.) which in some instances may result in an initial increase in serum levels which will then be followed by a decrease after equilibration is reached.

There are indications that the larger the chromophore in the macrolide nucleus the more effective is the compound in altering lipid metabolism e.g., reducing blood cholesterol levels. Therefore commensurate with the desideratum of obtaining the highest degree of effectiveness of the compositions of this invention, it is preferred to use the heptaene macrolide compounds.

It is also indicated that cleavage or other alteration of the macrolide nucleus which opens the lactone ring will destroy the activity of the compounds as will alteration of the chromophore present in the nucleus by total hydrogenation.

Since no one of the substituents found in the polyenic macrolide compounds such as amino sugars, aromatic amines, carboxyls, carbonyls, methyls, aliphatics, epoxies, etc., occur in all of the polyenic macrolide compounds described herein, indications are that these substituents, except for the hydroxyl function, are not essential for altering lipid metabolism, but rather that the active structure is the macrolide ring containing a conjugated chromophore portion (lipophilic section) and the flexible hydrophilic portion.

It is preferred, commensurate with the desideratum of obtaining the highest degree of effectiveness of the compositions of this invention per given dose of active ingredient, to use an enteric tablet or capsule. Thus when using a specific known polyene macrolide compound in the form of an enteric solid, the entire compound will remain intact when it reaches the intestinal tract so long as the enteric coating composition retains its integrity in the stomach. On the other hand, administration of the same dose in a standard solid pharmaceutical formulation may result in a cleavage of any amino sugar present, or of other groups similarly sensitive to gastric conditions. Such cleavage may further result in alteration of the polyenic macrolide nucleus, thereby diminishing the effectiveness of the active ingredient.

The effective dosage of the compounds of this invention depends upon the severity of condition, the stage and the individual characteristics of each mammal being treated. It is expected that the compositions will generally be administered in a dosage range from about 1 mg to about 100 mg active ingredient per kg of body weight per day and preferably from about 5 mg to about 40 mg per kg of body weight per day.

The compositions of this invention may in addition contain dietary supplements such as vitamins, choline, salts of glycerophosphoric acid and inositol, which are known to be effective in reducing serum cholesterol levels.

What is claimed is:

1. A process for treating hypercholesterolemia in a large mammal in need of said treatment which comprises orally administering an effective dose for treating hypercholesterolemia of N-acyl amphotericin B to said mammal.

2. The process of treating hypercholesterolemia as recited in claim 1 wherein said effective dose comprises from about 1 milligram to about 100 milligrams of N-acyl amphotericin B per kilogram of body weight per day.

3. The process of treating hypercholesterolemia as recited in claim 2 wherein said effective dose comprises from about 5 milligrams to about 40 milligrams of N-acyl amphotericin B per kilogram of body weight per day.

* * * * *